United States Patent [19]
Kang et al.

[11] Patent Number: 5,928,893
[45] Date of Patent: Jul. 27, 1999

[54] MONOCLONAL ANTIBODY SPECIFIC FOR HUMAN 4-1BB AND CELL LINE PRODUCING SAME

[75] Inventors: Chang-Yuil Kang; Joong-Gon Kim, both of Seoul, Rep. of Korea

[73] Assignee: LG Chemical Ltd., Seoul, Rep. of Korea

[21] Appl. No.: 08/737,560

[22] PCT Filed: Apr. 6, 1996

[86] PCT No.: PCT/KR96/00045

§ 371 Date: Nov. 13, 1996

§ 102(e) Date: Nov. 13, 1996

[87] PCT Pub. No.: WO96/32495

PCT Pub. Date: Oct. 17, 1996

[30] Foreign Application Priority Data

Apr. 8, 1995 [KR] Rep. of Korea ......................... 95/8176

[51] Int. Cl.[6] ........................... C12P 21/08; C12N 15/13; C07K 16/28
[52] U.S. Cl. ..................... 435/69.1; 435/70.21; 435/326; 435/346; 530/387.3; 530/388.1; 530/388.75
[58] Field of Search ............................... 530/387.3, 388.1, 530/388.75; 424/133.1, 141.1, 154.1; 435/69.1, 326, 346, 320.1, 70.21

[56] References Cited

U.S. PATENT DOCUMENTS 5,530,101  6/1996  Queen et al. .
5,674,704  10/1997  Goodwin et al. .

OTHER PUBLICATIONS

Kahan, B. Cur. Opin. Immunol. 4: 553–560, 1992.
Pollok, K. et al. J. Immunol. 150: 771–781, Feb. 1993.
Lenschow, D. et al. J. Exp. Med. 181: 1145–1155, Mar. 1995.

*Primary Examiner*—Christina Y. Chan
*Assistant Examiner*—Evelyn Rabin
*Attorney, Agent, or Firm*—Anderson, Kill & Olick, P.C.

[57] ABSTRACT

A monoclonal antibody specific for human 4-1BB, accessory molecule, selectively expressed on activated T cells; polynucleotides encoding the variable regions of the monoclonal antibody and amino acid sequences deduced therefrom; a hybridoma cell line producing the monoclonal antibody; and a process for preparing the hybridoma cell line.

6 Claims, 10 Drawing Sheets

FIG. 2A

AAC ATG AGA TCA CAG TTC TCT CTA CAG TTA CTG AGC ACA CAG GAC
CTC ACC <u>ATG GGA TGG AGC TAT ATC ATC CTC TTT TTG GTA GCA ACA</u>
<div align="center">Leader</div>

<u>GCT ACA GAT GTC CAC TCC</u> CAG GTC CAA CTG CAG CAG CCT GGG GCT
                                  Gln Val Gln Leu Gln Gln Pro Gly Ala

GAA CTG GTG AAG CCT GGG GCT TCA GTG AAG CTG TCC TGC AAG GCT
Glu Leu Val Lys Pro Gly Ala Ser Val Lys Leu Ser Cys Lys Ala

TCT GGC TAC ACC TTC AGC AGC TAC TGG ATG CAC TGG GTG AAG CAG
Ser Gly Tyr Thr Phe Ser <u>Ser Tyr Trp Met His</u> Trp Val Lys Gln
                                       CDR1

AGG CCT GGA CAA GTC CTT GAG TGG ATT GGA GAG ATT AAT CCT GGC
Arg Pro Gly Gln Val Leu Glu Trp Ile Gly <u>Glu Ile Asn Pro Gly</u>

AAC GGT CAT ACT AAC TAC AAT GAG AAG TTC AAG AGC AAG GCC ACA
<u>Asn Gly His Thr Asn Tyr Asn Glu Lys Phe Lys Ser</u> Lys Ala Thr
                        CDR2

CTG ACT GTA GAC AAA TCC TCC AGC ACA GCC TAC ATG CAA CTC AGC
Leu Thr Val Asp Lys Ser Ser Ser Thr Ala Tyr Met Gln Leu Ser

AGC CTG ACA TCT GAG GAC TCT GCG GTC TAT TAC TGT GCA AGA <u>TCT
Ser Leu Thr Ser Glu Asp Ser Ala Val Tyr Tyr Cys Ala Arg Ser

TTT ACT ACG GCA CGG GGG TTT GCT TAC</u> TGG GGC CAA GGG ACT CTG
<u>Phe Thr Thr Ala Arg Gly Phe Ala Tyr</u> Trp Gly Gln Gly Thr Leu
               CDR3

GTC ACT GTC TCT GCA <u>GCC AAA ACA ACA CCC CCA TCT GTC TAT CCA
Val Thr Val Ser Ala            Constant Region CTG G</u>

FIG. 2B

```
                              CDR1
4B4-1-1   QVQLQQPGAELVKPGASVKLSCKASGYTFSSYWMHWVKQRPGQVLEWIGE
                 *                         . *
ACL5'     QVQLQQSGAELVKPGASVKLSCKASGYTFTSYYMYWVKQRPGQGLEWIGE

CDR2
4B4-1-1   INPGNGHTNYNEKFKSKATLTVDKSSSTAYMQLSSLTSEDSAVYYCARSF
             *  **  .                                    .
ACL5'     INPSNGGINFNEKFKSKATLTVDKSSSTAYMQLSSLTSEDSAVYYCTRS-

CDR3
4B4-1-1   TTARGFA---YWGQGTLVTVS
           . *****        *
ACL5'     ----GYVRMDYWGQGTSVTVS
```

FIG. 3A

GAC ATT GTG ATG ACC CAG TCT CCA GCC ACC CAG TCT GTG ACT CCA
Asp Ile Val Met Thr Gln Ser Pro Ala Thr Gln Ser Val Thr Pro
                                +

GGA GAT AGA GTC TCT CTT TCC TGC AGG GCC AGC CAG ACT ATT AGC
Gly Asp Arg Val Ser Leu Ser Cys Arg Ala Ser Gln Thr Ile Ser
                                    ─────────────────────────
                                              CDR1
GAC TAC TTA CAC TGG TAT CAA CAA AAA TCA CAT GAG TCT CCA AGG
Asp Tyr Leu His Trp Tyr Gln Gln Lys Ser His Glu Ser Pro Arg
─────────────────

CTT CTC ATC AAA TAT GCT TCC CAA TCC ATC TCT GGG ATC CCC TCC
Leu Leu Ile Lys Tyr Ala Ser Gln Ser Ile Ser Gly Ile Pro Ser
                ───────────────────────────────
                            CDR2

AGG TTC AGT GGC AGT GGA TCA GGG TCA GAT TTC ACT CTC AGT ATC
Arg Phe Ser Gly Ser Gly Ser Gly Ser Asp Phe Thr Leu Ser Ile

AAC AGT GTG GAA CCT GAA GAT GTT GGA GTG TAT TAC TGT CAA GAT
Asn Ser Val Glu Pro Glu Asp Val Gly Val Tyr Tyr Cys Gln Asp
                                                    ────────
GGT CAC AGC TTT CCT CCG ACG TTC GGT GGA GGC ACC AAG CTG GAA
Gly His Ser Phe Pro Pro Thr Phe Gly Gly Gly Thr Lys Leu Glu
────────────────────────────
            CDR3

ATC AAA CGG GCT GAT GCT GCA CCA ACT GTA TCC ATC TTC CCA CCA
Ile Lys Arg Ala Asp Ala Ala Pro Thr Val Ser Ile Phe Pro Pro
            Constant Region

TCC

FIG. 3B

```
                          CDR1
4B4-1-1      DIVMTQSPATQSVTPGDRVSLSCRASQTISDYLHWYQQKSHESPRLLLIKY
                    *
VK23.32'CL   DIVMTQSPATLSVTPGDRVSLSCRASQSISDYLHWYQQKSHESPRLLLIKY

CDR2                                    CDR3
4B4-1-1      ASQSISGIPSRFSGSGSGSDFTLSINSVEPEDVGVYYCQDGHSFPPTFGG
               *   *                                *
VK23.32'CL   ASQSISGIPSSFRGSGSGSDFTLSINSVEPEDVGVYYCQNGHSFPP

4B4-1-1      GTKLEIK
```

MONOCLONAL ANTIBODY SPECIFIC FOR HUMAN 4-1BB AND CELL LINE PRODUCING SAME

FIELD OF THE INVENTION

The present invention relates to a monoclonal antibody (MAb) having an immunosuppressive activity, which is specific for human 4-1BB; a polynucleotide encoding the variable region thereof; and a hybridoma cell line producing same. More specifically, it pertains to a monoclonal antibody specific for human 4-1BB which is selectively expressed on activated T cells; polynucleotides encoding the variable regions of the monoclonal antibody and amino acid sequences deduced therefrom; a hybridoma cell line producing the monoclonal antibody; a process for preparing the cell line; and an immunosuppressive agent comprising the monoclonal antibody or a variant thereof.

BACKGROUND OF THE INVENTION

An immune response in human body is induced by a cascade of various processes which may be described as follows. First, an antigen is internalized through, e.g., phagocytosis, by antigen-presenting cells and degraded by cellular lysozyme, and the remainder forms a complex with a major histocompatibility complex(MHC) class II molecule. The resulting complex, after migrating to the outer surfaces of the antigen-presenting cell, is recognized by an antigen receptor of a helper T cell, triggering an antigen-specific humoral immune response. On the other hand, when an antigen, e.g., a viral antigen, is produced within a cell, it is degraded in the cell and the remainder forms a complex with a MHC class I molecule. The resulting complex moves to the outer surface of the virus-producing cell and an antigen-specific cellular immune response is initiated by the recognition of the complex by an antigen receptor of a cytotoxic T cell.

Subsequently, the T and antigen-presenting cells enter the initial stage of activation wherein new molecules, called accessory molecules, are expressed on their surfaces. The accessory molecules on the T cell bind to the corresponding ligand on the antigen-presenting cell and this binding accelerates the activation of the T and antigen-presenting cells, thereby promoting various immune responses. Representative accessory molecules include B7-1, B7-2, CD28, CTLA4, CD40, CD40 ligand, 4-1BB and 4-1BB ligand molecules(Goodwin et al., *Eur. J. Immunol.*, 23, 2631 (1993)).

The above-mentioned binding of accessory molecule, is indispensable for the activation of immune cells and, hence, the induction of an immune response. Accordingly, blocking of such binding may be decisive in suppressing immune responses. Further, immune responses may also be suppressed by depleting only the activated T cells which express the accessory molecules.

4-1BB, one of the accessory molecules mentioned above, was originally described as a protein expressed by activated murine T cells(Kwon, B. S., et al., *Proc. Natl. Acad. Sci. U.S.A.*, 84, 2896–2900(1987); and Kwon, B. S. and Weissman, S. M., *Proc. Natl. Acad. Sci. U.S.A.*, 86, 1963–1967(1989)) and subsequently demonstrated to encode a member of the tumor necrosis factor(TNF) receptor family of integral membrane proteins(Mallett, S. and Barclay, A. N., *Immunol. Today*, 12, 220–222(1991)). This receptor family is characterized by the presence of cysteine-rich motifs in the extracellular domains. Other members of this family include NGFR, CD40, OX-40, CD27, TNFR-I, TNFR-II, Fas and CD30(Smith, C. A., et al., *Cell*, 76, 959–962(1994); and Beutler, B. and VanHuffel, C., *Science*, 264, 667–668(1994)). 4-1BB is a 55 kDa homodimer and is expressed on a variety of murine T cell lines, thymocytes and mature T cells upon activation with concanavalin A(Con A), phytohemagglutinin(PHA) and ionomycin, or anti-CD3i (Kwon, B. S., et al., *Cell. Immunol.*, 121, 414–422(1989); and Pollok, K. E., et al., *J. Immunol.*, 150, 771–781(1993)). 4-1BB was found to be specifically coimmunoprecipitated with $p56^{lck}$ and to upregulate its own expression in Con A-stimulated thymocytes(Kim, Y. J., et al., *J. Immunol.*, 151, 1255–1262(1993)). These results suggest that 4-1BB plays a role in intracellular signalling.

Crosslinking of 4-1BB on the surface of mouse T cell with a monoclonal antibody(MAb) resulted in a several fold enhancement of T cell proliferation when activated suboptimally with anti-CD3i(Pollok et al., supra). The ligand for 4-1BB(4-1BBL) is found on activated macrophages and mature B cells(Goodwin, R. G., et al., *Eur. J. Immunol.*, 23, 2631–2641(1993); Pollok, K. E., et al., *Eur. J. Immunol.*, 24, 367–374(1994); and Alderson, M. R., et al., *Eur. J. Immunol.*, 24, 2219–2227(1994)). 4-1BBL shows homology to TNF, LT-A, LT-B, CD40L and CD27L, which form a merging family of molecules that bind to TNF receptor family members (Goodwin, et al., supra; and Alderson et al., supra). A recent study has shown that a 4-1BB-alkaline phosphatase fusion protein blocks T cell activation in the presence or absence of B7 molecules, providing an evidence for the importance of 4-1BB and 4-1BBL interaction in costimulation of T lymphocyte activation(DeBenedette, M. A., et al. *J. Exp. Med.*, 181, 985–992(1995)). The gene encoding human 4-1BB(h4-1BB) was recently isolated from a cDNA library of activated human peripheral T cells (Alderson, et al., supra) and the deduced amino acid sequence was shown to have 60% identity to murine 4-1BB with high conservation in the cytoplasmic domain.

On the other hand, success of an organ transplantation depends on how effectively the immunological rejection response of the organ recipient is suppressed against the transplanted organ. If the transplanted organ is not recognized by the recipient's immune system, it will function normally without the rejection problem. However, in most cases, the transplanted organ is recognized as a foreign antigen by the recipient's immune system and accordingly, immunosuppressive agents are normally used to prevent the rejection response. Exemplary immunosuppressive agents include cyclosporin, anti-lymphocyte globulin(ALG), anti-thymocyte globulin(ATG) and OKT3. However, these immunosuppressive agents tend to act not only on the activated immune cells but also on normal cells, causing serious adverse effects.

One of the most important functions of the immune system is to recognize self-antigens and discriminate them from foreign-antigens. Under normal physiological conditions, the immune system responds not to self antigens (the so-called "immunological tolerance") but only to foreign antigens. However, breakdown of the immunological tolerance may occur to produce an autoimmune response wherein the immune system recognizes self-antigens as foreign-antigens, thereby destroying self-antigens, and ultimately native cells, tissues and organs("autoimmune disease").

More than 30 diseases are known to be caused directly or indirectly by such autoimmune responses, and exemplary autoimmune diseases include rheumatoid arthritis, systemic lupus erythematosus, myasthenia gravis, glomerular nephritis, malignant aplastic anemia, thyroid diseases and testitis.

It is not clear at this time, exactly how such autoimmune diseases manifest themselves, and, accordingly, only limited, and after ineffective methods to treat autoimmune diseases are currently available, e. g., administration of an antiinflammatory agent to suppress inflammation caused by the autoimmune response, treatment with methotrexate which is cytotoxic to actively proliferating cells, radiotherapy or thoracic duct drainage to suppress excessive immune responses, and administration of immunosuppressive antilymphocyte serum(ASL) such as antilymphocyte globulin(ALG) and anti-thymocyte globulin(ATG). These treatments may show some short-term effectiveness, but they eventually damage normal immune calls in a long run.

Therefore, there has continued to exist a need to develop a safe immunosuppressive agent which acts selectively on activated immune cells without damaging normal immune cells.

SUMMARY OF THE INVENTION

Accordingly, it is an object of the present invention to provide a monoclonal antibody which is specific for an accessory molecule expressed on an activated immune cell.

Another object of the present invention is to provide polynucleotides encoding the variable regions of the monoclonal antibody and amino acid sequences encoded therein.

A further object of the present invention is to provide a hybridoma cell line capable of producing the monoclonal antibody and a process for preparing the cell line.

A still further object of the present invention is to provide an immunosuppressive agent comprising the monoclonal antibody or a variant thereof.

In accordance with one aspect of the present invention, there is provided a monoclonal antibody having a specificity for 4-1BB which is expressed on activated T cells and an immunosuppressive agent comprising the monoclonal antibody or a variant thereof.

BRIEF DESCRIPTION OF THE DRAWINGS

The above and other objects and features of the present invention will become apparent from the following description of the invention, when taken in conjunction with the accompanying drawings, in which:

FIG. 2A depicts the nucleotide sequence of the 4B4-1-1 $V_H$ gene and its deduced amino acid sequence (SEQ ID NO: 6); and FIG. 2B compares the amino acid sequence of the 4B4-1-1 $V_H$ gene (SEQ ID NO: 6) with that of the rheumatoid factor-binding antibody(A5'CL) (SEQ ID NO: 7);

FIG. 3A provides the nucleotide sequence of the 4B4-1-1 $V_L$ gene and its deduced amino acid sequence (SEQ ID NO: 8); and FIG. 3B compares the amino acid sequence of the 4B4-1-1 $V_L$ gene (SEQ ID NO: 8) with that of published, most homologous $V_L$ gene(VK23.32'CL) (SEQ ID NO: 9);

DETAILED DESCRIPTION OF THE INVENTION

Figure 1:
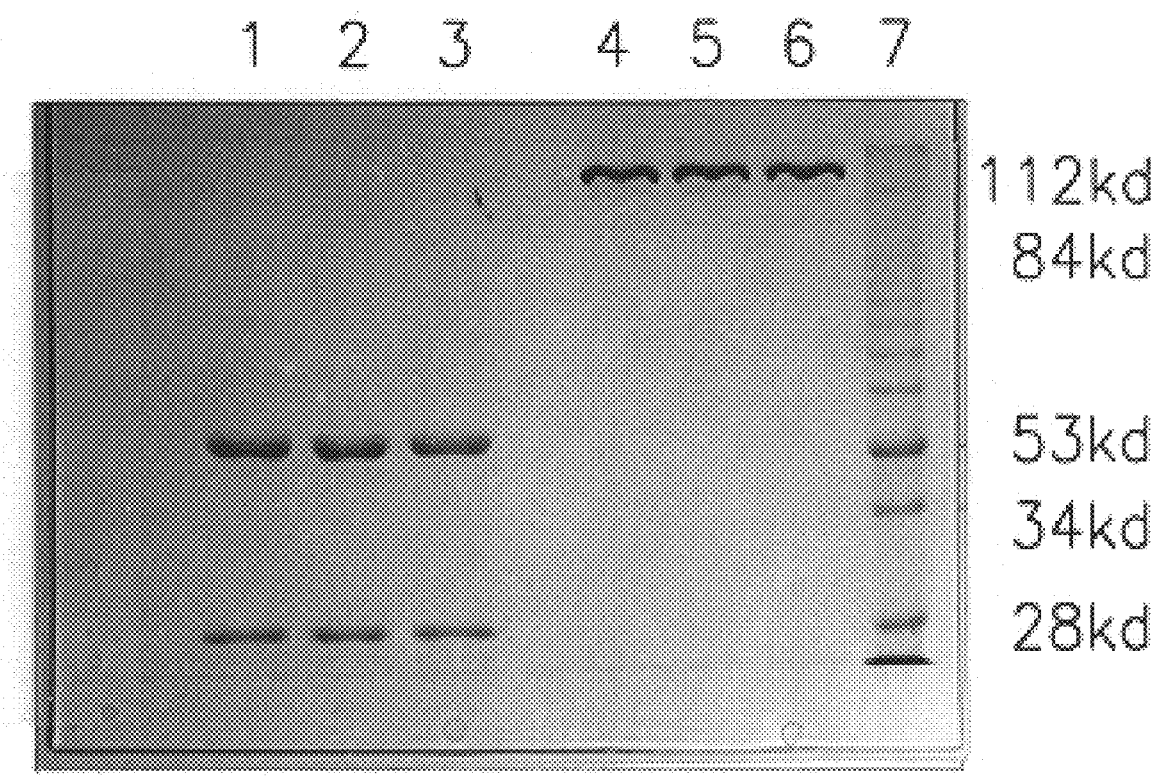
FIG. 1 shows the result of SDS-PAGE for confirming the purity of monoclonal antibody 4B4-1-1.

In accordance with one aspect of the present invention, there is provided a monoclonal antibody designated 4B4-1-1 which is specific for human 4-1BB expressed only or an activated human T cell.

The gene encoding the heavy chain variable region($V_H$) of MAb 4B4-1-1 comprises the 499 bp sequence shown in FIG. 2A and the deduced amino acid sequence thereof consists of a leader sequence of 19 amino acids, a typical mouse $V_H$ region(118 amino acids) and a part of the heavy chain constant region, containing all the conserved amino acid residues. Comparison of the amino acid sequence of the 4B4-1-1 $V_H$ region with those of ten murine $V_H$ groups (Kabat, E. A., et al., *Sequences of Immunological Interest*, 5th Ed., National Institutes of Health, Bethesla, 1991) indicates that the $V_H$ segment of 4B4-1-1 belongs to the subgroup II(B) and it is homologous with that of rheumatoid factor-binding antibody(A5'CL)(86.2% identity, 90.5% similarity; FIG. 2B). Most of the differences between the amino acid sequences of the $V_H$ segments of 4B4-1-1 and A5'CL lie in the hypervariable regions(CDR1, CDR2 and CDR3). Further, the D and $J_H$ segments of 4B4-1-1 are most closely related to DFL16.2 and $J_{H3}$, respectively.

The gene encoding the light chain variable region($V_L$) of MAb 4B4-1-1 comprises the 372 bp sequence shown in FIG. 3A and the deduced amino acid sequence thereof consists of the mouse immunoglobulin $V_L$ region(107 amino acids) and a part of the light chain constant region(14 amino acids). The deduced amino acid sequence of the $v_L$ gene indicates that the light chain of 4B4-1-1 belongs to the subgroup V and is very similar to VK23.32'CL(93.8% identity, 94.8% similarity; FIG. 3B) as well as that the $J_K$ segment is most close to MUSJK1.

The monoclonal antibody of the present invention may be prepared by transferring synthetic $V_H$ and $V_L$ genes, which are synthesized on the basis of the nucleotide sequence information as described above, into tumor cell lines and culturing the cell lines, or by culturing a hybridoma cell line which is produced by fusing a myeloma cell with spleen cells of a mouse immunized with $h_4$-1BB.

Specifically, the hybridoma cell line capable of producing a monoclonal antibody against h4-1BB may be prepared as follows.

1) Antigen Preparation

Human 4-1BB, which is used as an antigen in the present invention, may be prepared by a chemical peptide synthetic method as known in the art using the amino acid sequence described by Alderson, et al., supra, or by expressing a DNA coding for h4-1BB, which is synthesized chemically or separated from human body, in accordance with a genetic engineering technique. For instance, it may be prepared by constructing an expression vector containing the full length cDNA sequence encoding the human 4-1BB and the glutathionebinding domain of glutathione S-transferase(GST), expressing it in *E. coli* and purifying the resulting h4-1BB-GST fusion protein by using a suitable chromatographic column, e.g., Glutathione-Sepharose 4B column(Pharmacia LKB Biotechnology Inc.). The glutathione-binding domain may be cleaved from the fusion protein by using, e.g., factor Xa, and removed by using a Glutathione-Sepharose 4B column.

2) Immunization

Immunization of mice may be achieved by sequential injections of an immunogen, e.g., a cell containing h4-1BB or recombinant h4-1BB, to mice in accordance with a conventional method. For instance, a suitable amount of immunogen is injected intravenously, subcutaneously or intraperitoneally to mice and boosted twice or more at 2 or 3 week intervals to a total antigen amount of 100 to 200 μg/mouse. The injection may contain a suitable amount of Freund's complete or incomplete adjuvant, if necessary.

3) Cell Fusion

Three days after the final boost, spleen cells are separated from the immunized mouse and fused with myeloma cells, e.g., SP2/0-Ag14 myeloma cells(ATCC CRL 1581), in accordance with a conventional method, e.g., the method described by Mishell and Shiigi(*Selected Methods in Cellular Immunology*, W. H. Freeman & Company, 1980). The spleen cells and the myeloma cells may be used in a ratio ranging from 1:1 to 1:4. A fusion-promoting agent, e. g., polyethylene glycol(PEG) 4000, may be employed for accelerating the cell fusion. A exemplary medium suitable for use in the cell fusion step may be RPMI 1640(Gibco BRL Life Technologies Inc.) and the medium generally contains 10–15%(v/v) fetal bovine serum(FBS).

4) Selection of hybridoma Cell

The fused cells are cultured in a cell culture medium, e. g., RPMI1640 containing 15% FBS(Gibco BRL Life Technologies Inc.), supplemented with hypoxanthine, thymidine and aminopterin, and after seven to ten days, positive hybridoma clones producing antibodies specific for 4-1BB are selected by ELISA assay using the culture supernatant. Further, selection of positive clones may be accomplished by using a conventional method, e. g., limiting dilution technique, plaque method, spot method, agglutination assay and autoradiographic immunoassay.

One strain of such hybridoma cells producing antibodies specific for 4-1BB was designated as 4B4-1-1 and deposited on Mar. 21, 1995 with the Korean Collection for Type Cultures(KCTC)(Address: GERI, KIST, P.O. Box 115, Yusong, Taejon, 305-600, the Republic of Korea) with the accession number of KCTC 0157BP, under the terms of the Budapest Treaty on the International Recognition of the Deposit of Microorganism for the Purpose of Patent Procedure.

The monoclonal antibody of the present invention may be produced by culturing the hybridoma cell line in a suitable cell culture medium, e.g., RPMI 1640 medium, or by injecting the hybridoma cell line to Pristane®-injected mice and obtaining ascites from the mice. The monoclonal antibody can be purified from the culture supernatant or from the ascites obtained above in accordance with a conventional method, e.g., affinity column chromatography using protein A-Sepharose.

The binding affinity of the purified monoclonal antibody to Con A-activated T cells may be determined with flow cytometry, and the immunosuppressive activity thereof may be determined by using in vitro mixed lymphocyte reactions. The anti-4-1BB monoclonal antibody shows strong binding affinity to Con A-activated T cells and it has an immunosuppressive activity as is witnessed by its ability to suppress the lymphocyte proliferation in the in vitro mixed lymphocyte reaction.

Any variant of the present anti-4-1BB monoclonal antibody described above, which has high pharmaceutical efficacy, and at the same time, induces no or little anti-antibody reactions, may also fall in the scope of the present invention. Representatives of such variant may include a chimeric antibody and a humanized antibody.

The following Examples are intended to further illustrate the present invention without limiting its scope.

Further, percentages given below for solid in solid mixture, liquid in liquid, and solid in liquid are on a wt/wt, vol/vol and wt/vol basis, respectively, unless specifically indicated otherwise.

EXAMPLE 1

Preparation of Hybridoma Cell Line (Step 1) Preparation of Antigen

A pGEX-3X expression vector(Pharmacia LKB Biotechnology Inc.) containing the full length cDNA sequence encoding human 4-1BB and the glutathione-binding domain of glutathione S-transferase(GST) was constructed. *E. coli* was transformed with the vector and the transformant was cultured to express 4-1BB-GST fusion protein. The fusion protein was purified using a Glutathione-Sepharose 4B column(Pharmacia LKB Biotechnology Inc.).

(Step 2) Immunization

Eight to six-week-old female BALB/c mice(Laboratory Animal Center in Seoul National University, Seoul, Korea) were injected intraperitoneally with 20 μg of 4-1BB-GST suspended in 0.1 ml of complete Freund's adjuvant and boosted twice, each with 20 μg of 4-1BB-GST emulsified in incomplete Freund's adjuvant, at 3 week intervals.

Three days after the final boost, a small blood sample was taken from the tail of the immunized mouse and the titer of anti-4-1BB antibody was determined by ELISA in accordance with the method of Reference Example. When the antibody titer exceeded a certain value, spleen cells were separated from the immunized mouse for use in the cell fusion.

(Step 3) Cell Fusion

In accordance with the protocol described in Michell and Shiigi, supra, the spleen cells obtained in (Step 2) were mixed with SP2/0-Ag14 myeloma cells(ATCC CRL 1581) in a ratio of 1:2 in the presence of polyethylene glycol 4000(Gibco BRL Life Technologies Inc.).

After the fusion, cells were suspended in HAT medium (RPMI1640 medium containing 15% fetal bovine serum (FBS; Gibco BRL Life Technologies Inc.) supplemented with $1 \times 10^{-4}$ M hypoxanthine, $1.6 \times 10^{-5}$ M thymidine and $4 \times 10^{-7}$ M aminopterin (Gibco BRL Life Technologies Inc.)), placed in a 96-well microincubation tray and then cultured in an incubator at 37° C. under an atmosphere of 5% $CO_2$. 6, 7 or 8 days after the fusion, one half of the culture medium was changed with a fresh medium. Proliferation of cells was observed under a reverse-phase microscope and, when the cells were sufficiently grown, an ELISA assay was carried out using the supernatant taken from the 96-well microincubation tray.

(Step 4) Selection of Hybridoma Cell Line

Wells of Immulon II plate(Nunc Inc.) were coated overnight at 4° C. with 0.1 ml of phosphate-buffered saline (PBS, pH 7.2) containing 200 ng of 4-1BB-GST. The wells were washed three times with PBS and blocked for 1 hour with PBS containing 1% bovine serum albumin at room temperature.

100 μl/well of hybridoma culture supernatant obtained in (Step 3), which is mixed with 1% bovine serum albumin in PBS, was added to the wells and the plate was incubated for 2 hours.

The plate was washed several times with PBS and 0.1 ml of 1000-fold diluted alkaline phosphatase-conjugated goat anti-mouse Ig(Southern Biotechnology Associates Inc.) was added to each well and the plate was left standing for 2 hours. The wells were washed with PBS for several times, and a substrate solution(pH 9.6), which was prepared by dissolving disodium p-nitrophenyl phosphate in a carbonate buffer to a concentration of 1 mg/ml(Sigma Chemical Co.), was added to the wells in an amount of 0.1 ml/well. The plate was left standing for 10 minutes and the optical density (O.D.) of the sample at 405 nm was read on an Emax microplate reader(Molecular Devices).

The cells in wells showing positive results in the above ELISA were transferred to a 24-well plate and then cultured. To investigate whether the cell culture has binding affinity to 4-1BB, the same ELISA procedure as above was repeated using 4-1BB-GST fusion protein and 4-1BB. The binding activity of the antibody in the cell culture supernatant was represented by O.D. at 405 nm of the sample in ELISA, while bovine serum albumin(BSA) was employed as a control. The result is shown in Table I.

TABLE I

| coating protein | 4-1BB-GST | 4-1BB | BSA |
|---|---|---|---|
| O.D. (Binding Activity) | 2.30 | 2.43 | 0.06 |

As shown in Table I, the hybridoma cell culture reacts specifically with 4-1BB.

To select the hybridoma cells producing an antibody which acts specifically on 4-1BB, the culture supernatant was diluted to a concentration of one cell/well and the plate was cultured at the same condition as above for 10 days. A cell line producing antibody having a specificity to 4-1BB molecule was confirmed with ELISA and designated as 4B4-1. A subcloning in accordance with the same method as above gave a cell line 4B4-1-1 which produces anti-4-1BB monoclonal antibody.

Hybridoma cell line 4B4-1-1 was deposited on Mar. 21, 1995 with the Korean Collection for Type Cultures(KCTC) (Address: GERI, KIST, P.O. Box 115, Yusong, Taejon, 305-600, the Republic of Korea) under the accession number of KCTC 0157BP.

EXAMPLE 2

Preparation of Antibody by Using the Hybridoma Cell Line $1 \times 10^6$ 4B4-1-1 hybridoma cells were injected to the eritoneum of a BALB/c mouse treated with 0.5 ml of Pristane® (2,6,10,14-tetramethylpentadecane, Sigma Chemical Co.). 10 days later, ascites was recovered from the mouse. The ascites was subjected to affinity chromatography on a protein-A Sepharose CL-4B column(Pharmacia LKB Biotechnology Inc.) to purify the monoclonal antibody. The amount of the monoclonal antibody was approximately 1 mg/ml ascites.

The characteristics of the monoclonal antibody were determined with an antibody analysis kit(Cal biochem. Cat. No. 386445) and, as a result, it was found that the monoclonal antibody of the present invention is IgGI and has an isotype of kappa light chain.

Further, the antibody was subjected to sodium dodecyl sulfate-polyacrylamide gel electrophoresis(SDS-PAGE) and then stained with coomassie blue, in accordance with the method of W. K. Laemmli(*Nature*, 227, 680(1970)). The result is shown in FIG. 1, wherein the observed strong bands correspond to the heavy and light chains of IgG. This result shows that the monoclonal antibody is pure. In FIG. 1, lanes 1 to 3 show the heavy and light chains of monoclonal antibody 4B4-1-1; lanes 4 to 6, the entire monoclonal antibody 4B4-1-1; and lane 7, a standard molecular weight marker.

EXAMPLE 3

Nucleotide and Amino Acid Sequence Analysis

Total RNA was isolated from $1 \times 10^8$ 4B4-1-1 hybridoma cells prepared in Example 2 by using the guanidium isothiocyanate-CsCl gradient method(Chirgwin, J. J., et al., *Biochemistry*, 18, 5294–5299(1979)). RNA pellet was resolved in diethylpyrocarbonate(DEPC)-treated water and treated with RNase-free DNase(Boehringer-Mannheim Co.). mRNA was isolated using QuickPrep Micro mRNA Purification Kit (Pharmacia LKB Biotechnology Inc.). cDNA was prepared from about 5 μg of total RNA or 25 ng of mRNA by using MMLV(Moloney murine leukemia virus) reverse transcriptase (Boehringer-Mannheim Co.) in accordance with the manufacturer's instruction together with $C_y$ or $C_k$ primer(Korea Biotech. Inc.; Table 2). Prepared cDNA was purified by phenol/chloroform extraction, followed by ethanol precipitation.

To amplify the heavy chain variable region($V_H$) gene, a (dG)s tail was added to the 3'-terminus of the cDNA by terminal deoxynucleotidyl transferase(Boehringer-Mannheim Co.). The CDNA template was amplified by polymerase chain reaction(PCR) of 50 μl scale by repeating 35 times the thermal cycle of: 1 min. at 94° C., 2 min. at 55° C., and 3 min. at 72° C. $C_y$ primer, which is complementary to the sequence of the constant region of γ chain($C_y$) genes, and $(dC)_{17}$ oligomer, which is complementary to the dG-tail, were used as primers for PCR. 1 μl aliquot of first-round PCR product was reamplified by repeating 25 times the same thermal cycle as above.

To prepare the light chain variable region($V_L$) gene, a cDNA was synthesized and amplified by repeating 35 times the thermal cycle as above under the same condition. $C_x$ primer, which is complementary to the sequence of the constant region of κ chain($C_κ$) gene, and N4 or N6 primers, which is complementary to the DNA sequence of N-termini of $C_K$ chains, were employed as primers for PCR(Table II). The PCR products were resolved on 2% agarose gel, and desired DNA bands were excised, electroeluted, and then cloned into pCR™II vector using TA Cloning Kit (Invitrogen).

TABLE II

| Primer | Priming Region | Sequence |
|---|---|---|
| $C_γ$ | γ chain constant domain (114–124)* | 5'-CCAGTGGATAGAC(C/A/T)GATGG GG(G/C)TGT(TC)GTTTTGGC-3' (SEQ ID NO:1) |
| $C_κ$ | κ chain constant domain (112–121)* | 5'-GGATGGTGGGAAGATGGATACAGTT GGTGC-3' (SEQ ID NO:2) |
| N4 | κ chain variable domain(1–8)* (Group I)** | 5'-GACATTGTGATG(A/T)C(A/T)C AGTCTCCA-3' (SEQ ID NO:3) |
| N6 | κ chain variable domain(1–8)* (Group V)** | 5'-GA(C/T)AT(T/C)GTGATGACCC AGTC(C/T)C(A/C)(A/C)-3' (SEQ ID NO:4) |
| N21 | κ chain variable domain(1–7)* (Group V)** | 5'-GACATTGT(G/A)ATGAC(A/T/C) CAGTCT-3' (SEQ ID NO:5) |

*Amino acid number of mouse γ or κ chain(Kabat, et al., supra).
**Mouse κ chain group(Kabat, et al., supra).

Template plasmid DNA was purified using Magic™ Minipreps DNA purification system(Promega Biotec), and sequenced by the dideoxy chain termination method by using a Sequenase version 2.0 reagent Kit(Amersham) and primers SP6 and T7(Pro:mega Biotec). The DNA sequences were analyzed using PCGENE software, Blast database, and referring to a reference, i.e., Kabat, E. A., et al., *Sequences of Proteins of Immunological Interest*, 1991).

(1) $V_H$ of MAb 4B4-1-1

The $V_H$ cDNA of MAb 4B4-1-1 was prepared from total RNA and cloned by the anchored PCR method(Ohara, O., et al., *Proc. Natl. Acad. Sci., U.S.A.,* 86, 6883–6887(1989)) using a downstream primer($C_\gamma$ primer) that hybridizes to the constant region and an upstream primer(($dC$)$_{17}$) that hybridizes to the dG-tail. DNA sequencing revealed that the $V_H$ CDNA of MAb 4B4-1-1 contained 499 bp, but no dg-tail was found at the end of this fragment(FIG. 2A) (SEQ ID NO: 6). The deduced amino acid sequence of the gene revealed a leader sequence of 19 amino acids, a typical mouse $V_H$ region(118 amino acid) and a part of the heavy chain constant region, containing all the conserved amino acid residues.

Comparison of the amino acid sequence of the 4B4-1-1 $V_H$ region with the sequence of ten murine $V_H$ groups (Kabat, et al., supra) indicated that the $V_H$ segment of 4B4-1-1 belongs to the subgroup II(B), and a homology search of GenBank database revealed that it has the highest homology with that of rheumatoid factor-binding antibody (A5'CL) (SEQ ID NO: 7) (86.2% identity, 90.5% similarity; FIG. 2B). Most of the amino acid differences between the VH segments of 4B4-1-1 and A5'CL were found in the hypervariable regions(CDR1, CDR2 and CDR3). The sequence data also indicated that the D and $J_H$ segments of 4B4-1-1 are most closely related to DFL16.2 and $J_{H3}$.

FIG. 2A shows the nucleotide sequence of the 4B4-1-1 $V_H$ gene and its deduced amino acid sequence. Complementary determining regions(CDRs) and numbering of the amino acid are as defined by Kabat, et al., supra. CDRs are shown by solid lines under the appropriate amino acid residues. A short segment of the constant region is also shown, and primer regions used for PCR are shaded.

FIG. 2B shows $V_H$ gene amino acid sequences of 4B4-1-1 and rheumatoid factor-binding antibody(A5'CL). Unrelated residues of the two proteins are marked by '*'; similar residues are marked by '.'; and CDRs are shaded.

(2) VL of MAb 4B4-1-1

The VL cDNA of MAb 4B4-1-1 was prepared from total mRNA of hybridoma 4B4-1-1 and cloned by the PCR method with primer N4 or N6. The nucleotide sequencing of the PCR products revealed that the DNA fragments obtained from PCRs with N4 or N6 primer are composed of 363 bp and identical to each other(FIG. 3A) (SEQ ID NO: 9).

Deduced amino acid sequences of this gene indicated that it contains the sequences of the mouse immunoglobulin $V_L$ region(107 amino acids) and a part of the light chain constant region(14 amino acids). The deduced amino acid sequence of the VL gene indicated that the light chain of 4B4-1-1 belongs to the subgroup V and is very similar to VK23.32'CL (SEQ ID NO: 9) (93.8% identity, 94.8% similarity; FIG. 3B) as well as that the $J_\kappa$ segment is very close to MUSJK1.

Since the $V_L$ gene of 4B4-1-1 was cloned by PCR using a primer corresponding to N-terminus, the first 24 nucleotides of this gene were derived from the primer and may not be authentic. This could affect the antigen-binding activity of a chimeric antibody of 4B4-1-1. Thus, we determined the amino acid sequence of the first 8 residues, which turned out to be consistent with that deduced from the nucleotide sequence, except that the last residue was proline instead of glutamine. Replacement of glutamine with proline would result in an antigen-binding site having different structure. To confirm the above result, the $v_L$ gene was cloned using a shorter primer, N21(Table II). The cloned gene contained CCA as a codon for the 8th amino acid position, which is indeed translated into proline.

FIG. 3A represents the nucleotide sequence of the 4B4-1-1 $V_L$ gene and its deduced amino acid sequence. 't' indicates the 8th amino acid residue which was Q in the $V_L$ gene cloned using N6 primer, while other markings have the same meanings as defined for FIG. 2A. FIG. 3B displays the deduced amino acid sequences of the 4B4-1-1 $V_L$ gene and the published homologous $V_L$ gene(VK23.32'CL), wherein other markings have the same meanings as defined for FIG. 2B.

Test Example 1: Reaction of Activated T Cells with MAb 4B4-1-1

20 ml of venous blood sample, which was taken from a healthy adult, was put into a sterilized tube containing heparin and mixed immediately with the same volume of PBS(pH 7.2). 3 ml of HISTOPAQUE-1077(Sigma Chemical Co.) was added to a 15 ml tube and left standing at room temperature. Then, 6 ml of the mixture of venous blood and PBS was piled carefully up on HISTOPAQUE-1077 layer and the tube was centrifuged at room temperature, 400×g for 30 min.

Subsequently, the lymphocytes collected at the interface of the HISTOPAQUE-1077 and serum layers were recovered by using a pipette and placed in a 15 ml tube. 10 ml of PBS was added to the tube and centrifuged at 250×g for 10 min. The precipitated cells were mixed well with 10 mR of PBS and then centrifuged twice under the same condition as above to separate the peripheral blood lymphocytes(PBL).

To activate the lymphocytes, concanavalin A(Con A) was added in an amount of 10 μg/ml per $2\times10^6$ cells/ml of the lymphocyte and the mixture was incubated for a certain period. The Con A-activated lymphocytes were stained with trypan blue and the number of cells was determined by microscopical examination.

Monoclonal antibody 4B4-1-1 was added to the cells in an amount of 50 μl/$2\times10^6$ cells and the mixture was reacted at 4° C. for 30 min. The reaction mixture was then washed twice with PBS containing 2% bovine serum albumin and thereto was added 20 μl of fluorescein isothiocyanate (FITC)-conjugated goat anti-mouse Ig(Becton Dickinson), followed by incubating the mixture at 4° C. for 30 min. in the dark. The resulting product was washed twice with PBS containing 2% bovine serum albumin. 20 μl of R-phycoerythrine(RPE)-conjugated mouse anti-human CD4$^+$ T MAb(Dako, Carpinteria) or mouse anti-human CD8$^+$ T MAb(Serotec, Oxford) was added thereto and the mixture was incubated at 4° C. for 30 min. The resulting product was washed twice with PBS containing 2% bovine serum albumin and the lymphocytes were fixed with 1% formaldehyde and analyzed with FACStar plus flow cytometer(Becton Dickinson) to investigate the staining appearances of the lymphocytes. The result is shown in FIGS. 4 and 5.

Figure 4A:
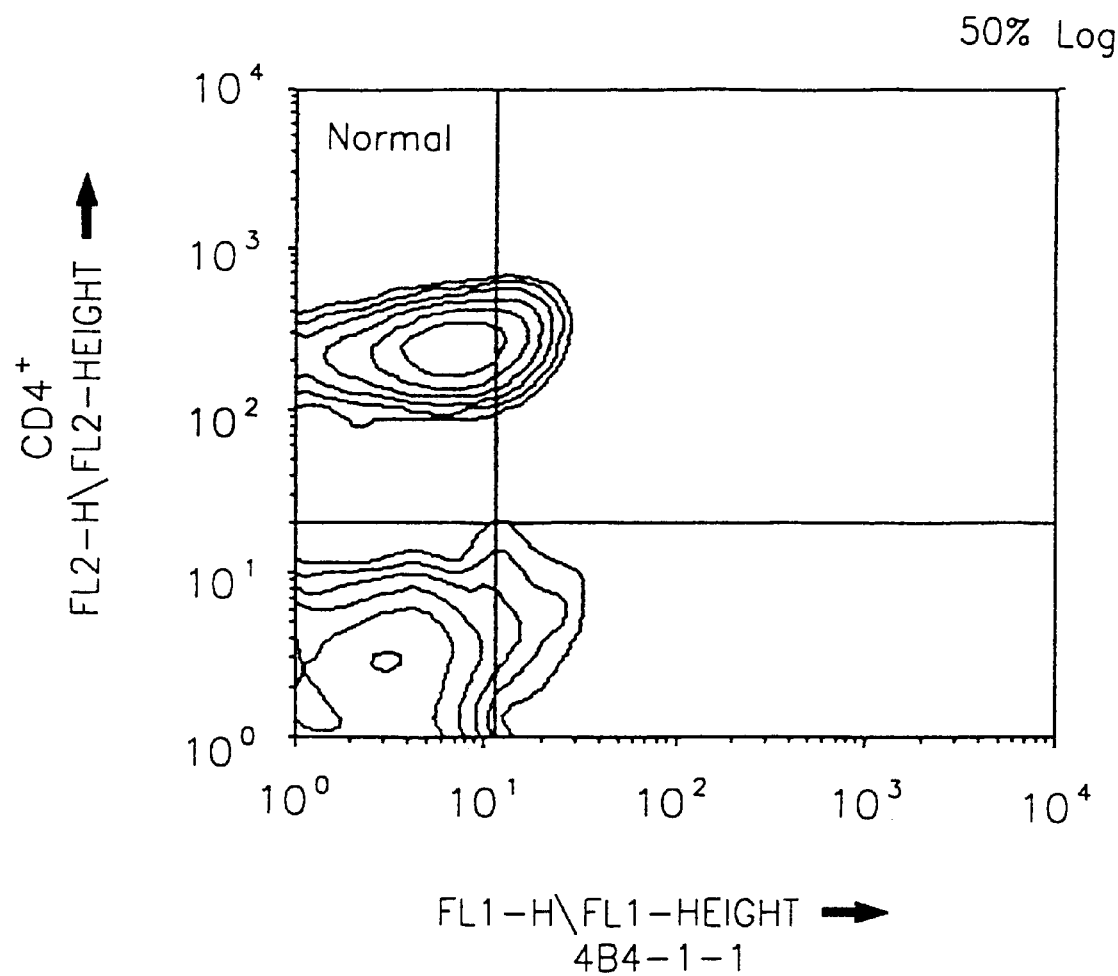
FIG. 4 presents the specificity of MAb 4B4-1-1 for normal human CD4$^+$ T cells and for activated human CD4$^+$ T cells stimulated with Con A for 24 hours, respectively.
Figure 4B:
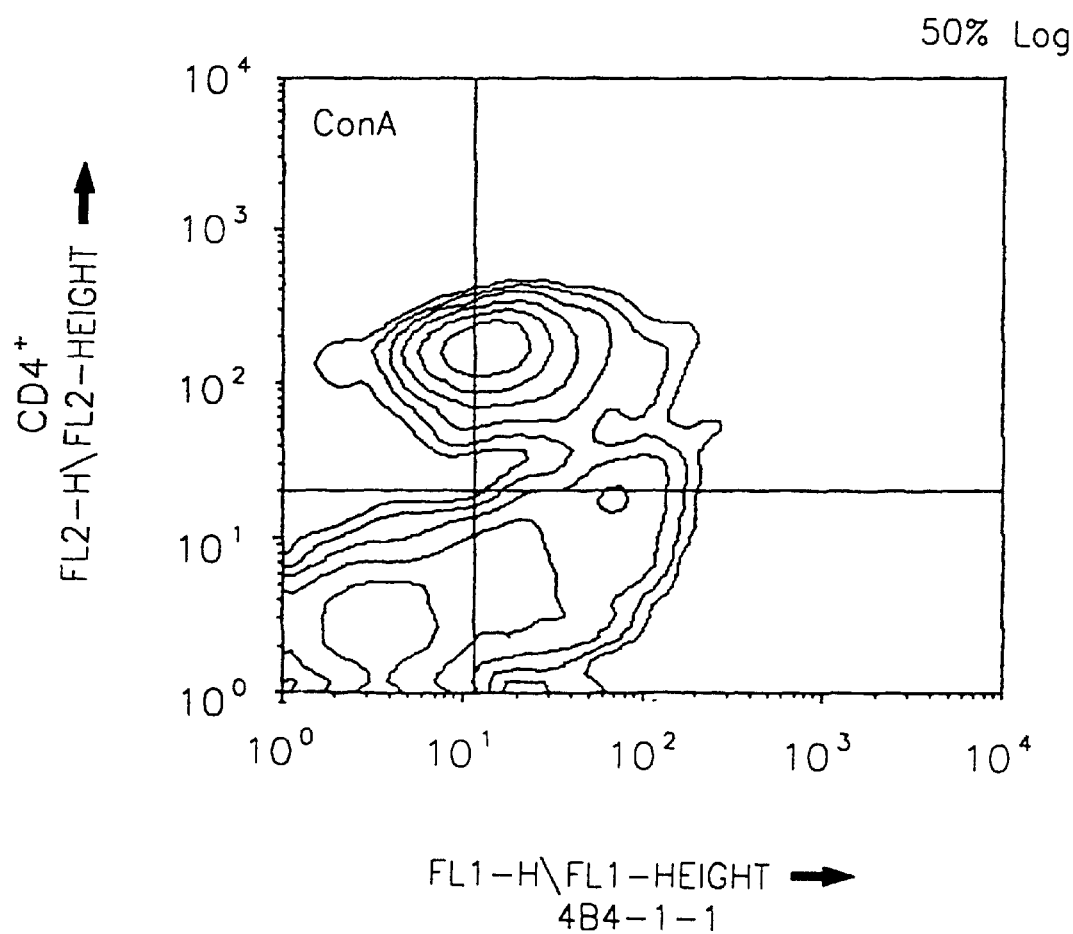

FIG. 4A shows the reactivity of normal CD4$^+$ T cells with MAb 4B4-1-1, wherein 17% of the CD4$^+$ T cells show positive responses, and FIG. 4B presents the reactivity of CD4$^+$ T cells, which were activated with Con A for 24 hours, with MAb 4B4-1-1, wherein 72% of the CD4$^+$ cells show positive responses.

Figure 5A:
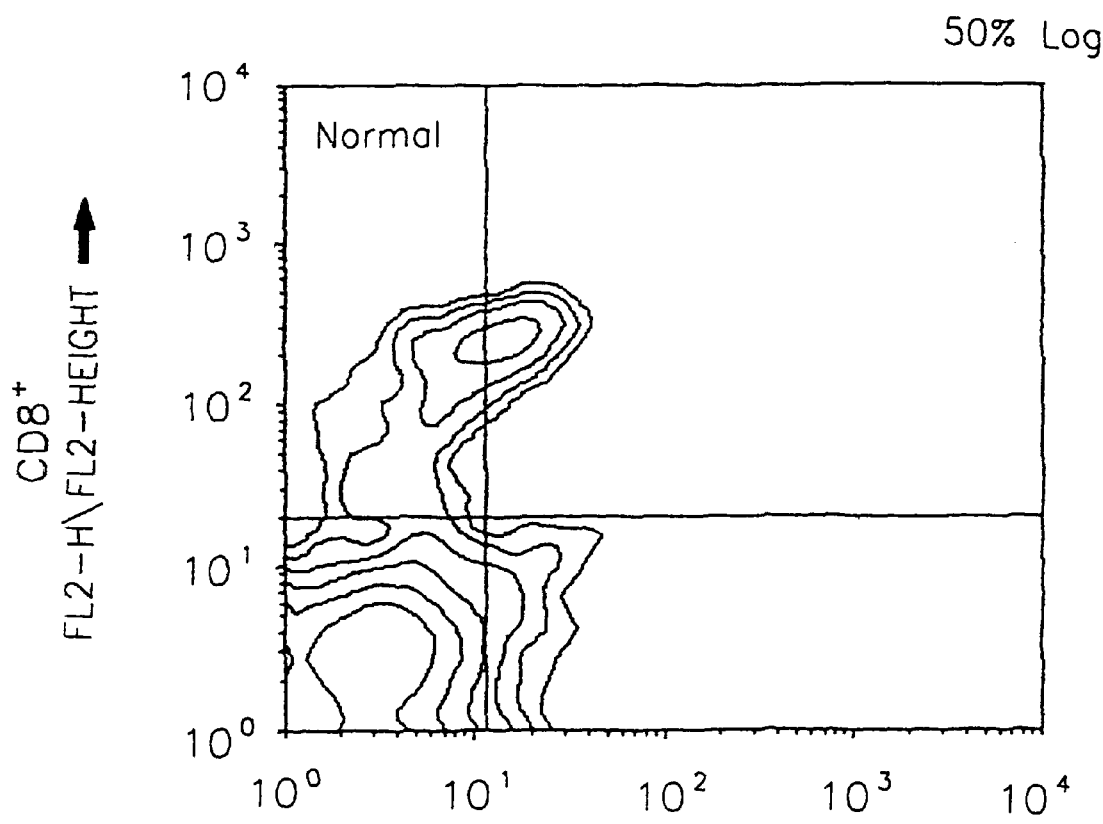
FIG. 5 exhibits the specificity of MAb 4B4-1-1 for normal human CD8$^+$ T cells and for activated human CD8$^+$ T cells stimulated with Con A for 24 hours, respectively.
Figure 5B:
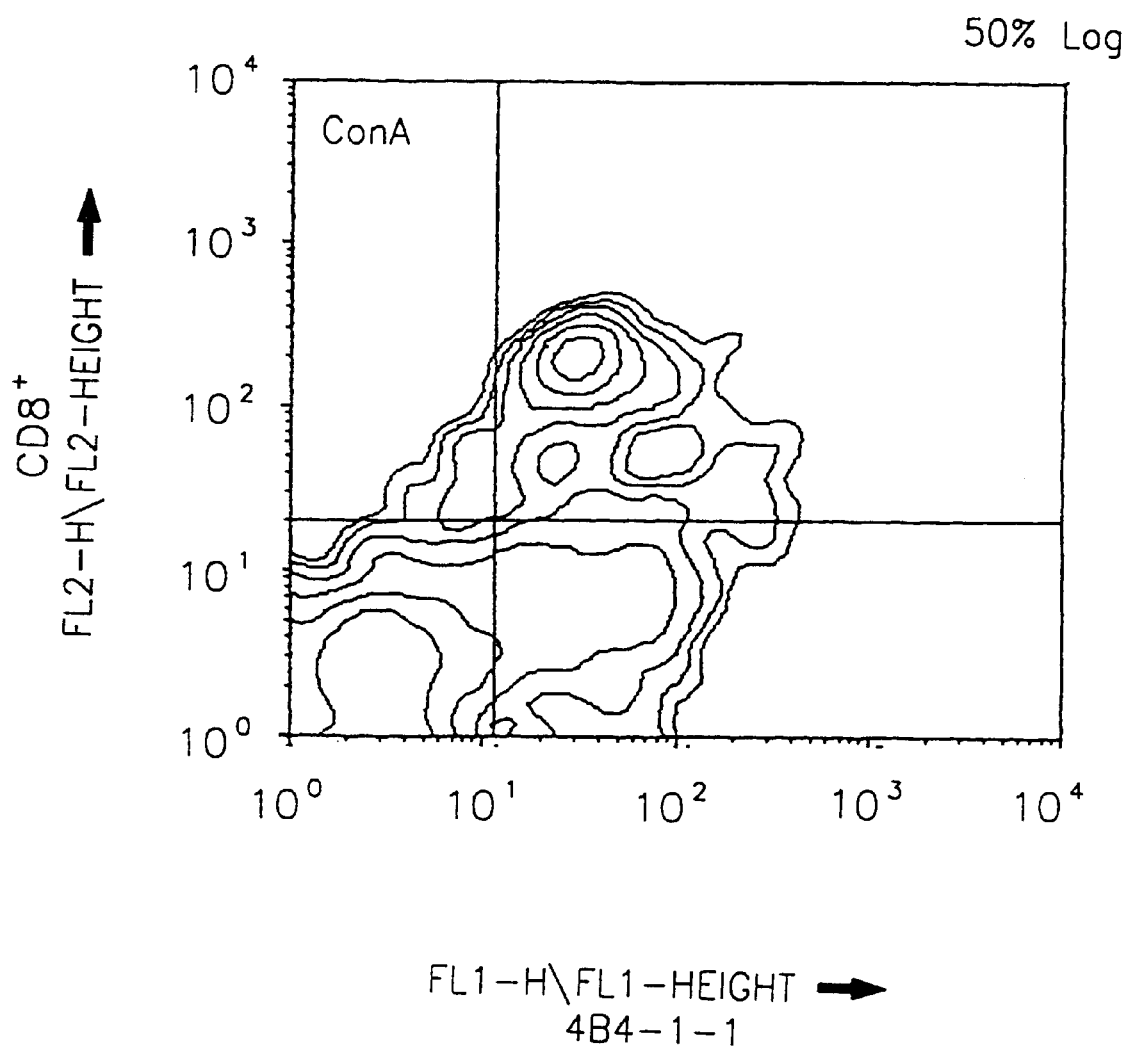

FIG. 5A represents the reactivity of normal CD8$^+$ T cells with MAb 4B4-1-1, wherein 36% of the CD8$^+$ T cells show positive responses, and FIG. 5B exhibits the reactivity of CD8$^+$ T cells, which were activated with Con A for 24 hours, with MAb 4B4-1-1, wherein 89% of the CD8$^+$ T cells show positive responses.

As can be seen from the above results, activated CD4$^+$ and CD8$^+$ T cells show much higher response to MAb 4B4-1-1 than the non-activated normal T cells.

Test Example 2: In vitro test for immunosuppressive activity of MAb 4B4-1-1

Two samples of peripheral blood lymphocytes(PBL) were obtained from persons in accordance with the same procedure as in Test Example 1.

1×10⁵ cells from one person were mixed with 3000 rad-irradiated 1×10⁵ cells from another person. The mixed cells were placed in the wells of a 96-well culture plate, and 4B4-1-1 was added to each well to a concentration of 0, 0.15, 0.6, 2.5, 10 or 40 μg/m². The plate was incubated for 7 or 9 days and the proliferation of cells in each well was determined as follows. 1 μCi of ³H-thymidine was added to each well and the plate was incubated for 8 hours. The cells were collected on a glass filter membrane and the membrane was placed in a 5 m² scintillation vial. 2.5 m² of the scintillation cocktail was added to the vial and cpm of ³H-thymidine was determined by using a β-counter. The suppression rate(%) was calculated as follows:

$$\text{Suppression rate (\%)} = \left(1 - \frac{\text{CPM of mixed lymphocytes incubated with MAb 4B4-1-1}}{\text{CPM of mixed lymphocytes incubated without MAb 4B4-1-1}}\right) \times 100$$

Figure 6:
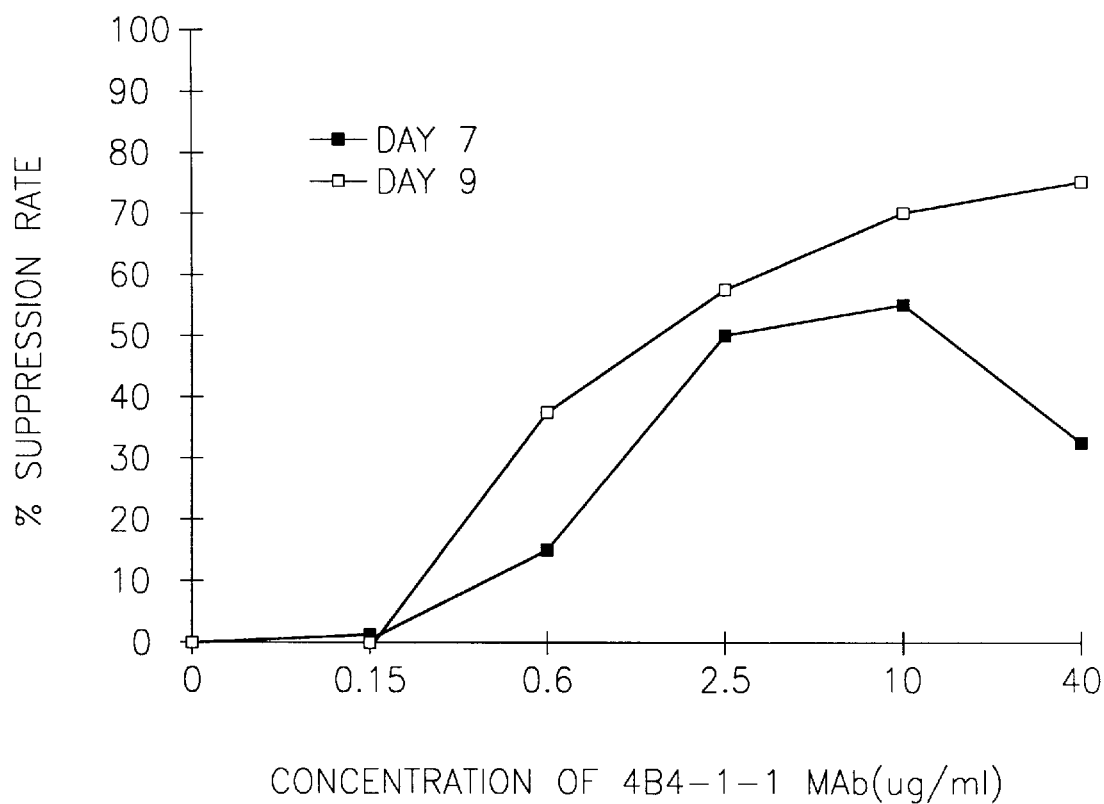
FIG. 6 illustrates the suppressive effect of Mab 4B4-1-1 on the one way-allogeneic mixed lymphocyte reaction which was carried out for 7 or 9 days.

FIG. 6 illustrates the suppression effect of MAb 4B4-1-1 on the one way-allegeneic mixed lymphocyte reaction which was carried out for 7(—■—) or 9(—□—) days and was suppressed by addition of 10 μg/ml MAb 4B4-1-1 by 52% or 67%. This result demonstrates that the monoclonal antibody of the present invention, i.e., MAb 4B4-1-1 has a significant immunosuppressive activity.

Test Example 3: Specificity of MAb 4B4-1-1 for Synovial T cells of Rheumatoid Arthritis Patient 20 ml of synovial fluid, which was taken from the knee joint of a rheumatoid arthritis patient, was put into a sterilized tube containing heparin and the tube was centrifuged at room temperature, 400×g for 10 min. The precipitated cells were suspended in distilled water for 10 min. to remove red blood cells. Synovial lymphocytes thus obtained were stained with trypan blue to count the number of cells.

On the other hand, peripheral blood lymphocytes(PBL) were obtained from a rheumatoid arthritis patient in accordance with the same procedures as in Test Example 1.

Monoclonal antibody 4B4-1-1 was added to the arthrosynovial lymphocytes or PBL in an amount of 50 μl/2× 10⁶ cell and the mixture was reacted at 4° C. for 30 min. When the reaction was completed, the resulting product was washed twice with PBS containing 2% bovine serum albumin. 20 μl of fluorescein isothiocyanate(FITC)-conjugated goat anti-mouse Ig(Becton Dickinson) was added to the product and the mixture was incubated at 4° C. for 30 min. in the dark. The resulting product was washed twice with PBS containing 2% bovine serum albumin and 20 μl of R-phycoerythrine(RPE)-conjugated mouse anti-human CD4⁺ T MAb(Dako, Carpinteria) or mouse anti-human CD8⁺ T MAb(Serotec, Oxford) was added thereto. The mixture was incubated at 4° C. for 30 min. in the dark. The resulting product was washed twice with PBS containing 2% bovine serum albumin and the lymphocytes were fixed with 1% formaldehyde and analyzed with FACStar plus flow cytometer(Becton Dickinson) to investigate the staining appearances of the monocytes. The result is shown in Table 3.

TABLE 3

| | % of T Cells Showing Reactivity with 4B4-1-1 | | | |
|---|---|---|---|---|
| | PBL | | Synovial lymphocyte | |
| | CD4⁺ T Cell | CD8⁺ Cell | CD4⁺ T Cell | CD8⁺ T Cell |
| Patient 1 | 2.2 | 12.69 | 11.30 | 68.08 |
| Patient 2 | 20.0 | 43.53 | 37.97 | 42.44 |

As can be seen from Table 3, the cells capable of reacting with MAb 4B4-1-1 are more abundant in the peripheral blood T cells than in the arthrosynovial T cells. Namely, most T cells of arthrosynovial lymphocytes from an arthritis patient can bind to MAb 4B4-1-1. Accordingly, rheumatoid arthritis can be treated by administering MAb 4B4-1-1 or its variant to the rheumatoid arthritis patient, thereby removing cells binding to MAb 4B4-1-1.

As described above, anti-h4-1BB monoclonal antibody can suppress various immune responses by inhibiting the function of activated T cells with blocking the 4-1BB molecule, or by removing activated T cells expressing 4-1BB molecule. Therefore, the monoclonal antibody of the present invention may be used as an immunosuppressive agent for the treatment of various autoimmune diseases and preventing the rejection response after the organ transplantation.

While the invention has been described with respect to the above specific embodiments, it should be recognized that various modifications and changes may be made to the invention by those skilled in the art which also fall within the scope of the invention as defined by the appended claims.

SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: primer C (xi) SEQUENCE DESCRIPTION: SEQ ID NO: 1:

CCAGTGGATA GACHGATGGG GSTGTYGTTT TGGC        34

(2) INFORMATION FOR SEQ ID NO: 2:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: primer C (xi) SEQUENCE DESCRIPTION: SEQ ID NO: 2:

GGATGGTGGG AAGATGGATA CAGTTGGTGC        30

(2) INFORMATION FOR SEQ ID NO: 3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: primer N4

(xi) SEQUENCE DESCRIPTION: SEQ ID NO: 3:

GACATTGTGA TGWCWCAGTC TCCA        24

(2) INFORMATION FOR SEQ ID NO: 4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: primer N6

(xi) SEQUENCE DESCRIPTION: SEQ ID NO: 4:

GAYATYGTGA TGACCCAGTC YCMM        24

(2) INFORMATION FOR SEQ ID NO: 5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: primer N21

(xi) SEQUENCE DESCRIPTION: SEQ ID NO: 5:

GACATTGTRA TGACHCAGTC T        21

(2) INFORMATION FOR SEQ ID NO: 6:

(i) SEQUENCE CHARACTERISTICS:
(A) LENGTH: 454 base pairs
(B) TYPE: nucleic acid
(C) STRANDEDNESS: single
(D) TOPOLOGY: linear (ii) MOLECULE TYPE: DNA (ix) FEATURE:
(D) OTHER INFORMATION: 7 to 63 bp leader sequence
64 to 420 bp 4B4-1-1 heavy chain variable region
154 to 168 bp hypervariable region CDR1
211 to 261 bp hypervariable region CDR2
358 to 387 bp hypervariable region CDR3
421 to 454 bp 4B4-1-1 heavy chain constant region (xi) SEQUENCE DESCRIPTION: SEQ ID NO: 6:

```
AAC ATG AGA TCA CAG TTC TCT CTA CAG TTA CTG AGC ACA CAG GAC              45

GCT ACA GAT GTC CAC TCC CAG GTC CAA CTG CAG CAG CCT GGG GCT              90
                        Gln Val Gln Leu Gln Gln Pro Gly Ala
                         1               5

GAA CTG GTG AAG CCT GGG GCT TCA GTG AAG CTG TCC TGC AAG GCT             135
Glu Leu Val Lys Pro Gly Ala Ser Val Lys Leu Ser Cys Lys Ala
 10              15                  20

TCT GGC TAC ACC TTC AGC AGC TAC TGG ATG CAC TGG GTG AAG CAG             180
Ser Gly Tyr Thr Phe Ser Ser Tyr Trp Met His Trp Val Lys Gln
 25              30                  35

AGG CCT GGA CAA GTC CTT GAG TGG ATT GGA GAG ATT AAT CCT GGC             225
Arg Pro Gly Gln Val Leu Glu Trp Ile Gly Glu Ile Asn Pro Gly
 40              45                  50

AAC GGT CAT ACT AAC TAC AAT GAG AAG TTC AAG AGC AAG GCC ACA             270
Asn Gly His Thr Asn Tyr Asn Glu Lys Phe Lys Ser Lys Ala Thr
 55              60                  65

CTG ACT GTA GAC AAA TCC TCC AGC ACA GCC TAC ATG CAA CTC AGC             315
Leu Thr Val Asp Lys Ser Ser Ser Thr Ala Tyr Met Gln Leu Ser
 70              75                  80

AGC CTG ACA TCT GAG GAC TCT GCG GTC TAT TAC TGT GCA AGA TCT             360
Ser Leu Thr Ser Glu Asp Ser Ala Val Tyr Tyr Cys Ala Arg Ser
 85              90                  95

TTT ACT ACG GCA CGG GGG TTT GCT TAC TGG GGC CAA GGG ACT CTG             405
Phe Thr Thr Ala Arg Gly Phe Ala Tyr Trp Gly Gln Gly Thr Leu
100             105                 110

GTC ACT GTC TCT GCA GCC AAA ACA ACA CCC CCA TCT GTC TAT CCA             450
Val Thr Val Ser Ala
115

CTG G                                                                   454
```

(2) INFORMATION FOR SEQ ID NO: 7:

(i) SEQUENCE CHARACTERISTICS:
(A) LENGTH: 116 amino acids
(B) TYPE: amino acid
(D) TOPOLOGY: linear (ii) MOLECULE TYPE: protein (ix) FEATURE:
(D) OTHER INFORMATION: rheumatoid factor-binding antibody(A5'CL)

(xi) SEQUENCE DESCRIPTION: SEQ ID NO: 7:

```
Gln Val Gln Leu Gln Gln Ser Gly Ala Glu Leu Val Lys Pro Gly
 1               5                  10                  15

Ala Ser Val Lys Leu Ser Cys Lys Ala Ser Gly Tyr Thr Phe Thr
                20                  25                  30
```

```
Ser Tyr Tyr Met Tyr Trp Val Lys Gln Arg Pro Gly Gln Gly Leu
            35                  40                  45

Glu Trp Ile Gly Glu Ile Asn Pro Ser Asn Gly Gly Ile Asn Phe
            50                  55                  60

Asn Glu Lys Phe Lys Ser Lys Ala Thr Leu Thr Val Asp Lys Ser
            65                  70                  75

Ser Ser Thr Ala Tyr Met Gln Leu Ser Ser Leu Thr Ser Glu Asp
            80                  85                  90

Ser Ala Val Tyr Tyr Cys Thr Arg Ser Gly Tyr Val Arg Met Asp
            95                  100                 105

Tyr Trp Gly Gln Gly Thr Ser Val Thr Val Ser
            110                 115
```

(2) INFORMATION FOR SEQ ID NO: 8:

(i) SEQUENCE CHARACTERISTICS:
        (A) LENGTH: 363 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION:  1 to 324 bp 4B4-1-1 light chain
            variable region
            70 to 102 bp hypervariable region CDR1
            148 to 168 bp hypervariable region CDR2
            265 to 291 bp hypervariable region CDR3
            325 to 363 bp 4B4-1-1 light chain constant region (xi) SEQUENCE DESCRIPTION: SEQ ID NO: 8:

```
GAC ATT GTG ATG ACC CAG TCT CCA GCC ACC CAG TCT GTG ACT CCA        45
Asp Ile Val Met Thr Gln Ser Pro Ala Thr Gln Ser Val Thr Pro
 1               5                  10                  15

GGA GAT AGA GTC TCT CTT TCC TGC AGG GCC AGC CAG ACT ATT AGC        90
Gly Asp Arg Val Ser Leu Ser Cys Arg Ala Ser Gln Thr Ile Ser
                 20                  25                  30

GAC TAC TTA CAC TGG TAT CAA CAA AAA TCA CAT GAG TCT CCA AGG       135
Asp Tyr Leu His Trp Tyr Gln Gln Lys Ser His Glu Ser Pro Arg
                 35                  40                  45

CTT CTC ATC AAA TAT GCT TCC CAA TCC ATC TCT GGG ATC CCC TCC       180
Leu Leu Ile Lys Tyr Ala Ser Gln Ser Ile Ser Gly Ile Pro Ser
                 50                  55                  60

AGG TTC AGT GGC AGT GGA TCA GGG TCA GAT TTC ACT CTC AGT ATC       225
Arg Phe Ser Gly Ser Gly Ser Gly Ser Asp Phe Thr Leu Ser Ile
                 65                  70                  75

AAC AGT GTG GAA CCT GAA GAT GTT GGA GTG TAT TAC TGT CAA GAT       270
Asn Ser Val Glu Pro Glu Asp Val Gly Val Tyr Tyr Cys Gln Asp
                 80                  85                  90

GGT CAC AGC TTT CCT CCG ACG TTC GGT GGA GGC ACC AAG CTG GAA       315
Gly His Ser Phe Pro Pro Thr Phe Gly Gly Gly Thr Lys Leu Glu
                 95                  100                 105

ATC AAA CGG GCT GAT GCT GCA CCA ACT GTA TCC ATC TTC CCA CCA       360
Ile Lys Arg Ala Asp Ala Ala Pro Thr Val Ser Ile Phe Pro Pro

TCC                                                                363
```

(2) INFORMATION FOR SEQ ID NO: 9:

(i) SEQUENCE CHARACTERISTICS:
        (A) LENGTH: 96 amino acids
        (B) TYPE: amino acid
        (D) TOPOLOGY: linear

```
    (ii) MOLECULE TYPE: protein (ix) FEATURE:
         (D) OTHER INFORMATION: VK23.32'CL (xi) SEQUENCE DESCRIPTION: SEQ ID NO: 9:

Asp Ile Val Met Thr Gln Ser Pro Ala Thr Leu Ser Val Thr Pro
 1               5                  10                  15

Gly Asp Arg Val Ser Leu Ser Cys Arg Ala Ser Gln Ser Ile Ser
                20                  25                  30

Asp Tyr Leu His Trp Tyr Gln Gln Lys Ser His Glu Ser Pro Arg
                35                  40                  45

Leu Leu Ile Lys Tyr Ala Ser Gln Ser Ile Ser Gly Ile Pro Ser
                50                  55                  60

Ser Phe Arg Gly Ser Gly Ser Gly Ser Asp Phe Thr Leu Ser Ile
                65                  70                  75

Asn Ser Val Glu Pro Glu Asp Val Gly Val Tyr Tyr Cys Gln Asn
                80                  85                  90

Gly His Ser Phe Pro Pro
                95

(2) INFORMATION FOR SEQ ID NO: 10:

(i) SEQUENCE CHARACTERISTICS:
        (A) LENGTH: 119 amino acids
        (B) TYPE: amino acid
        (D) TOPOLOGY: linear (ii) MOLECULE TYPE: protein (ix) FEATURE:
         (D) OTHER INFORMATION: 4B4-1-1 heavy chain variable region (xi) SEQUENCE DESCRIPTION: SEQ ID NO: 10:

Gln Val Gln Leu Gln Gln Pro Gly Ala Glu Leu Val Lys Pro Gly
   1               5                  10                  15

Ala Ser Val Lys Leu Ser Cys Lys Ala Ser Gly Tyr Thr Phe Ser
                  20                  25                  30

Ser Tyr Trp Met His Trp Val Lys Gln Arg Pro Gly Gln Val Leu
                  35                  40                  45

Glu Trp Ile Gly Glu Ile Asn Pro Gly Asn Gly His Thr Asn Tyr
                  50                  55                  60

Asn Glu Lys Phe Lys Ser Lys Ala Thr Leu Thr Val Asp Lys Ser
                  65                  70                  75

Ser Ser Thr Ala Tyr Met Gln Leu Ser Ser Leu Thr Ser Glu Asp
                  80                  85                  90

Ser Ala Val Tyr Tyr Cys Ala Arg Ser Phe Thr Thr Ala Arg Gly
                  95                  100                 105

Phe Ala Tyr Trp Gly Gln Gly Thr Leu Val Thr Val Ser Ala
                  110                 115

(2) INFORMATION FOR SEQ ID NO: 11:

(i) SEQUENCE CHARACTERISTICS:
        (A) LENGTH: 108 amino acids
        (B) TYPE: amino acid
        (D) TOPOLOGY: linear (ii) MOLECULE TYPE: protein (ix) FEATURE:
         (D) OTHER INFORMATION: 4B4-1-1 light chain variable region
```

(xi) SEQUENCE DESCRIPTION: SEQ ID NO: 11:

```
Asp Ile Val Met Thr Gln Ser Pro Ala Thr Gln Ser Val Thr Pro
 1               5                  10                  15

Gly Asp Arg Val Ser Leu Ser Cys Arg Ala Ser Gln Thr Ile Ser
                20                  25                  30

Asp Tyr Leu His Trp Tyr Gln Gln Lys Ser His Glu Ser Pro Arg
                35                  40                  45

Leu Leu Ile Lys Tyr Ala Ser Gln Ser Ile Ser Gly Ile Pro Ser
                50                  55                  60

Arg Phe Ser Gly Ser Gly Ser Gly Ser Asp Phe Thr Leu Ser Ile
                65                  70                  75

Asn Ser Val Glu Pro Glu Asp Val Gly Val Tyr Tyr Cys Gln Asp
                80                  85                  90

Gly His Ser Phe Pro Pro Thr Phe Gly Gly Gly Thr Lys Leu Glu
                95                 100                 105

Ile Lys Arg
```

(2) INFORMATION FOR SEQ ID NO: 12:

(i) SEQUENCE CHARACTERISTICS:
        (A) LENGTH: 357 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: polynucleotide encoding 4B4-1-1 heavy
            chain variable region (xi) SEQUENCE DESCRIPTION: SEQ ID NO: 12:

```
CAG GTC CAA CTG CAG CAG CCT GGG GCT GAA CTG GTG AAG CCT GGG        45

GCT TCA GTG AAG CTG TCC TGC AAG GCT TCT GGC TAC ACC TTC AGC        90

AGC TAC TGG ATG CAC TGG GTG AAG CAG AGG CCT GGA CAA GTC CTT       135

GAG TGG ATT GGA GAG ATT AAT CCT GGC AAC GGT CAT ACT AAC TAC       180

AAT GAG AAG TTC AAG AGC AAG GCC ACA CTG ACT GTA GAC AAA TCC       225

TCC AGC ACA GCC TAC ATG CAA CTC AGC AGC CTG ACA TCT GAG GAC       270

TCT GCG GTC TAT TAC TGT GCA AGA TCT TTT ACT ACG GCA CGG GGG       315

TTT GCT TAC TGG GGC CAA GGG ACT CTG GTC ACT GTC TCT GCA           357
```

(2) INFORMATION FOR SEQ ID NO: 13:

(i) SEQUENCE CHARACTERISTICS:
        (A) LENGTH: 324 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: polynucleotide encoding 4B4-1-1
            light chain variable region (xi) SEQUENCE DESCRIPTION: SEQ ID NO: 13:

```
GAC ATT GTG ATG ACC CAG TCT CCA GCC ACC CAG TCT GTG ACT CCA        45

GGA GAT AGA GTC TCT CTT TCC TGC AGG GCC AGC CAG ACT ATT AGC        90

GAC TAC TTA CAC TGG TAT CAA CAA AAA TCA CAT GAG TCT CCA AGG       135
```

-continued

| | |
|---|---|
| CTT CTC ATC AAA TAT GCT TCC CAA TCC ATC TCT GGG ATC CCC TCC | 180 |
| AGG TTC AGT GGC AGT GGA TCA GGG TCA GAT TTC ACT CTC AGT ATC | 225 |
| AAC AGT GTG GAA CCT GAA GAT GTT GGA GTG TAT TAC TGT CAA GAT | 270 |
| GGT CAC AGC TTT CCT CCG ACG TTC GGT GGA GGC ACC AAG CTG GAA | 315 |
| ATC AAA CGG | 324 |

What is claimed is:

1. A monoclonal antibody having a specificity for human 4-1BB, wherein the heavy chain and light chain variable regions thereof have the amino acid sequences of SEQ ID NOs: 10 and 11, respectively.

2. The monoclonal antibody of claim 1 wherein the heavy chain and light chain variable regions thereof are encoded in the nucleotide sequences of SEQ ID NOs: 12 and 13, respectively.

3. A chimeric variant of the monoclonal antibody of claim 1.

4. A hybridoma cell line which produces a monoclonal antibody having a specificity for human 4-1BB, wherein the heavy chain and light chain variable regions thereof have the amino acid sequences of SEO ID Nos. 10 and 11, respectively.

5. The hybridoma cell line of claim 4, which is 4B4-1-1 (KCTC 0157BP).

6. A process for preparing a hybridoma cell line capable of producing a monoclonal antibody having a specifity for human 4-1 BB, wherein the heavy chain and light chain variable regions thereof have the amino acid sequences of SEO ID Nos. 10 and 11, respectively, the process comprising recovering spleen cells from a mouse immunized with human 4-1 BB, fusing the spleen cells with mycloma cells, and culturing the fused cells.

* * * * *